(12) United States Patent
Gerlitz et al.

(10) Patent No.: US 9,681,832 B2
(45) Date of Patent: Jun. 20, 2017

(54) MEASUREMENT APPARATUSES AND METHODS USING A COMBINED SUBSTANCE COOLING DEVICE

(71) Applicant: GlucoVista, Inc., Fairfield, NJ (US)

(72) Inventors: Yonatan Gerlitz, Herzliya (IL); Meir Shitrit, Talpiot Jerusalem (IL)

(73) Assignee: GlucoVista Inc., Fairfield, NJ (US)

( * ) Notice: Subject to any disclaimer, the term of this patent is extended or adjusted under 35 U.S.C. 154(b) by 241 days.

(21) Appl. No.: 14/312,464

(22) Filed: Jun. 23, 2014

(65) Prior Publication Data

US 2014/0371552 A1 Dec. 18, 2014

Related U.S. Application Data

(63) Continuation-in-part of application No. 12/883,063, filed on Sep. 15, 2010, which is a continuation-in-part (Continued)

(51) Int. Cl.
*A61B 5/1455* (2006.01)
*A61B 5/1491* (2006.01)
(Continued)

(52) U.S. Cl.
CPC ............ *A61B 5/1491* (2013.01); *A61B 5/01* (2013.01); *A61B 5/1455* (2013.01);
(Continued)

(58) Field of Classification Search
CPC ..... A61B 5/002; A61B 5/0059; A61B 5/1455; A61B 5/14551; A61B 5/14532;
(Continued)

(56) References Cited

U.S. PATENT DOCUMENTS 5,461,867 A * 10/1995 Scudder ............... A47J 36/28
126/263.1
5,900,632 A * 5/1999 Sterling ............... G01N 21/71
250/252.1
(Continued)

FOREIGN PATENT DOCUMENTS

JP H0298358 4/1990

OTHER PUBLICATIONS

International Search Report and Written Opinion for PCT/US2014/043716 dtd Jan. 9, 2015, Jan. 9, 2015.
(Continued)

*Primary Examiner* — Eric Winakur
*Assistant Examiner* — Chu Chuan (J J) Liu
(74) *Attorney, Agent, or Firm* — Parsons, Behle & Latimer (57) ABSTRACT

A measurement apparatus includes a cooling device including two separated, different substances exhibiting an endothermic reaction when combined to decrease a temperature of the cooling device and a contacting mechanism to contact an assay surface with the cooling device. The apparatus includes a temperature measurement device to measure a temperature of the assay surface and an infrared radiation detector to measure infrared radiation emitted or absorbed. A data processor is configured to determine a concentration of a substance in the subject's body using the measured temperature and the infrared radiation. A measurement method includes using the cooling device and decreasing a temperature of the assay surface to a lower temperature, then measuring a temperature of the assay surface during an increase of the temperature. An infrared radiation detector measures infrared radiation emitted from or absorbed by the assay surface during the temperature increase from the lower temperature.

16 Claims, 7 Drawing Sheets

Related U.S. Application Data of application No. 12/607,903, filed on Oct. 28, 2009, now Pat. No. 8,611,975, which is a continuation-in-part of application No. 12/101,859, filed on Apr. 11, 2008, now Pat. No. 8,401,604.

(60) Provisional application No. 61/838,329, filed on Jun. 23, 2013.

(51) Int. Cl.
  *A61B 5/01* (2006.01)
  *A61F 7/10* (2006.01)
  *A61B 5/145* (2006.01)

(52) U.S. Cl.
  CPC ...... *A61B 5/14532* (2013.01); *A61B 5/14546* (2013.01); *A61F 7/10* (2013.01)

(58) Field of Classification Search
  CPC ... A61B 5/145302; A61B 5/0002; A61B 5/01; A61B 5/1491; A61B 5/14546
  USPC ........ 600/310, 316, 322, 331, 334, 340, 473
  See application file for complete search history.

(56) References Cited

U.S. PATENT DOCUMENTS

| | | | |
|---|---|---|---|
| 6,161,028 A * | 12/2000 | Braig | A61B 5/0059 |
| | | | 250/339.03 |
| 2006/0036304 A1* | 2/2006 | Cordani | A61F 7/03 |
| | | | 607/108 |
| 2007/0106139 A1* | 5/2007 | Nagata | A61B 5/01 |
| | | | 600/365 |
| 2009/0069741 A1 | 3/2009 | Altshuler et al. | |
| 2009/0149926 A1 | 6/2009 | Dacey, Jr. et al. | |
| 2009/0259407 A1* | 10/2009 | Gerlitz | A61B 5/14532 |
| | | | 702/19 |
| 2011/0004080 A1 | 1/2011 | Gerlitz et al. | |

OTHER PUBLICATIONS

International Searching Authority; Invitation to Pay Additional Fees issued in PCT/US2014/043716 dated Oct. 17, 2014.

* cited by examiner

MEASUREMENT APPARATUSES AND METHODS USING A COMBINED SUBSTANCE COOLING DEVICE

RELATED APPLICATION DATA

The present application claims the benefit of priority under 35 U.S.C. §119 to U.S. Provisional App. No. 61/838,329, filed Jun. 23, 2013, entitled "Special Cold Pack for Non-invasive Glucometer or other measurements of body substances". The present application is a continuation-in-part of U.S. patent application Ser. No. 12/883,063, filed Sep. 15, 2010, entitled "Method for Non-Invasive Analysis of a Substance Concentration Within a Body," which is a continuation-in-part of U.S. patent application Ser. No. 12/607,903, entitled "Apparatus and Method for Non-Invasive Measurement of a Substance Within a Body" and filed on Oct. 28, 2009, and Ser. No. 12/101,859, entitled "Apparatus and Methods for Non-Invasive Measurement of a Substance Within a Body" and filed on Apr. 11, 2008. Each of the indicated applications is incorporated herein by reference.

TECHNICAL FIELD

Apparatuses and methods herein pertain to measurement using a mixed substance cooling device, such as a cold pack, and infrared radiation and determining the concentration of a substance in a subject's body.

BACKGROUND

U.S. patent application Ser. No. 12/883,063, filed Sep. 15, 2010, and Ser. No. 12/101,859, filed Apr. 11, 2008, describe a method of non-invasive measurement of glucose or other body substances. That method includes the steps of:

1. Cooling the skin at the point of measurement;
2. Allowing the recovery of the skin temperature; and
3. Taking multiple measurements during the skin's temperature recovery to analyze the glucose concentration level in the blood (or other body substances).

Application Ser. No. 12/883,063 and 12/101,859 mention that any suitable cooling apparatus may be used, and include a Peltier element as one possibility, but lack the description of other means and methods to use for cooling.

BRIEF DESCRIPTION OF THE DRAWINGS

Some embodiments are described below with reference to the following accompanying drawings.

FIGS. 7A and B are perspective, cutaway views of the front-end holding mechanism that holds the cold pack and allows the insertion and removal of the cold pack. FIG. 7A shows the position of the cold pack that is inserted and pushed to the front of the mechanism to touch the subject's skin. FIG. 7B shows the position of the mechanism and cold pack when the cold pack is moved to the back of the mechanism for removal.

DETAILED DESCRIPTION

The apparatuses and methods herein relate to methods for non-invasive glucose measurement when the measurement is done after cooling the skin in the measured area and during the skin's recovery to its original temperature. This apparatus and method further disclose the means and method for cooling the skin.

This apparatus and method describes the special means of the device and the method to use to cool the skin before the commencement of the measurement.

The cooling element is a cold pack with special construction as shown in the Figures.

Known instant cold packs include two sealed plastic bags with one enclosed inside the other. The small interior bag usually contains water and has a perforation that allows breakage when pressure is applied. The external bag contains material (e.g., ammonium nitrate, calcium ammonium nitrate, or urea) that has an endothermic chemical reaction with water. When the two materials are mixed, the endothermic reaction causes a fast cooling (i.e., reduction) in the temperature of the cold pack. There are drawbacks to using this known instant cold pack configuration: (1) one has to aggressively shake the instant cold pack for a good mixture for the desired cooling effect; and (2) the instant cold pack is flexible and soft and cannot easily fit into a fixed location in the glucometer.

The cold pack herein has a solid structure with special edge for insertion in the glucometer. For an example, the cold pack may be made out of plastic material and may be made by vacuum forming techniques. The lower cavity contains the material for the endothermic reaction with water; the upper cavity contains water. The top part of the cold pack is shaped so that it has a "spring load" effect with one or more sharp daggers that puncture the cavity containing the water and then spring back to its original position. This allows the water to drain into the cavity containing the material for the endothermic chemical reaction, thereby reducing the need to aggressively shake the cold pack. A safety sticker may be applied to the top of the cold pack in order to reduce unwanted activation of the cold pack during handling and/or transportation.

Another part of this apparatus and method is the mechanism to position and hold the cold pack at the desired place for cooling by approximately 10° C. (18° F.) and the automatic removal of the cold pack while keeping the measuring device pointed and in focus with the cooled area. This mechanism is described in FIG. 2.

Figure 2:
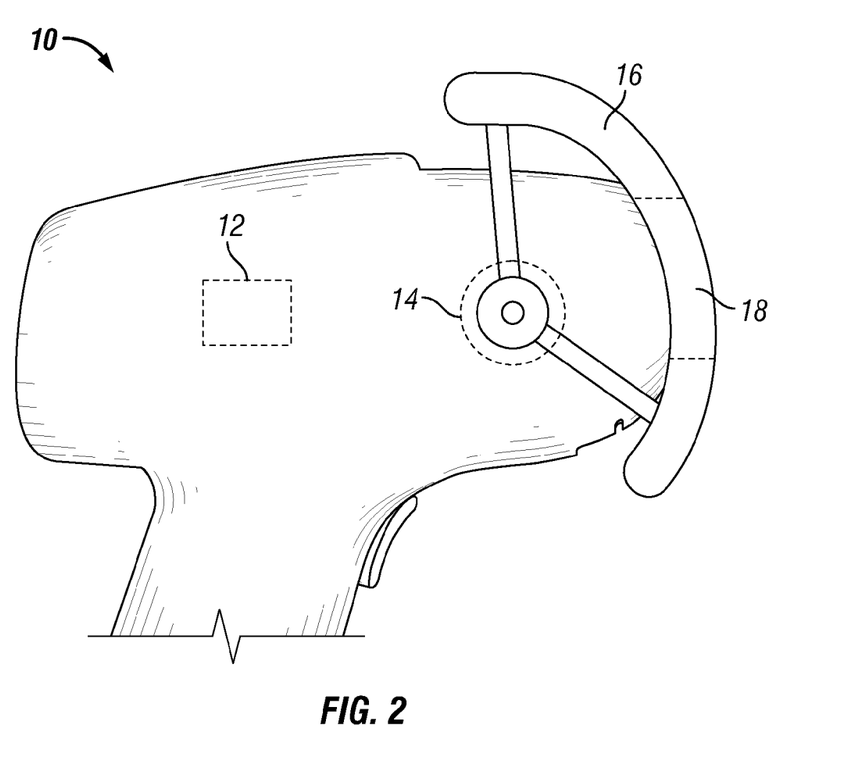
FIG. 2 is a schematic drawing of the assembly of the cold pack to the glucometer and the means to move it after cooling and to allow the measurement to commence.

FIG. 2 illustrates the glucometer and the cold pack holder at the front end of the glucometer. This holder, made from plastic material, forms an approximately 90° arc that has two parts: (1) the holder of the cold pack and (2) an aperture allowing a clear path for the infrared radiation. The front end of the plastic arc is designed to be on the focal plane of the glucometer's optical system. After activating the cold pack, the cold pack is inserted into one part of the plastic arc. The glucometer is activated and, after a predetermined time, the arc is moved by a motor or other means to introduce the aperture, thereby allowing the infrared information to reach the glucometer's optical system. In summary, the two goals of keeping the glucometer pointing at the cooled area and in focus with the cooled area are achieved by this simple structure.

Accordingly, a measurement apparatus described herein includes an infrared radiation detector, a cooling device, and a device configured to measure a surface temperature of a body. The cooling device includes a mixing mechanism configured to allow mixing two different substances exhibiting an endothermic reaction when mixed and a contacting mechanism configured to cool a surface of the body.

More specifically, another measurement apparatus includes a cooling device including two separated, different substances exhibiting an endothermic reaction when combined to decrease a temperature of the cooling device. A combining mechanism of the cooling device is configured to combine the two different substances. A contacting mechanism is configured to contact an assay surface of a subject's body with the cooling device and thereby to decrease a temperature of the assay surface of a subject's body to a lower temperature. A temperature measurement device is configured to measure a temperature of the assay surface of a subject's body during an increase of the temperature from the lower temperature. An infrared radiation detector is configured to measure infrared radiation emitted from or absorbed by the assay surface of a subject's body during the temperature increase. A data processor is configured to determine a concentration of a substance in the subject's body using the measured temperature of the assay surface and the measured infrared radiation.

By way of example, the processor may be configured to determine a rate of temperature change of the assay surface. Also, the processor may be configured to determine the concentration using the rate of temperature change as the measured temperature. The cooling device may include a rigid shell having a base, a lid that attaches to the base, and an opening through the lid. A flexible bag may have a size and shape configured to fit within the shell with the lid closed and expose the bag above the opening through the lid, the bag containing a first of the two different substances. A pouch within the flexible bag may contain a second of the two different substances, the pouch being configured to release the second substance into the first substance upon opening the pouch.

Also, a measurement method described herein includes mixing two different substances that react endothermically, decreasing a temperature of a cooling device using the mixed substances, and contacting a surface of a body with the cooling device. The method includes decreasing a temperature of the surface of the body and measuring infrared radiation absorbed or emitted from the body during recovery of the temperature. The concentration of a substance in the body is determined using the measured infrared radiation.

More specifically, another measurement method includes using a cooling device including two separated, different substances exhibiting an endothermic reaction when combined. The method includes combining the two different substances using a combining mechanism of the cooling device and decreasing a temperature of the cooling device using the combined substances. Using a contacting mechanism, an assay surface of a subject's body is contacted with the cooling device, thereby decreasing a temperature of the assay surface of the subject's body to a lower temperature. After decreasing the temperature of the assay surface using the cooling device, the method includes using a temperature measurement device and measuring a temperature of the assay surface of the subject's body during an increase of the temperature of the assay surface from the lower temperature. Using an infrared radiation detector, infrared radiation emitted from or absorbed by the assay surface is measured during the temperature increase from the lower temperature. Using a data processor, a concentration of a substance in the subject's body is determined using the measured temperature of the assay surface and the measured infrared radiation.

Further, a cooling device includes a rigid shell including a base, a lid that attaches to the base, and an opening through the lid. A flexible bag has a size and shape configured to fit within the shell with the lid closed and expose the bag above the opening through the lid, the bag containing a first of the two different substances. A pouch within the flexible bag contains a second of the two different substances, the pouch being configured to release the second substance into the first substance upon opening the pouch. The cooling device includes a mounting edge on opposing sides of the rigid shell, the mounting edge being configured to mount the cooling device to a measurement apparatus in a position.

By way of example, the mounting edge may include a circumferential flange of the lid and a circumferential flange of the base, the two flanges coinciding with one another with the lid closed.

Figure 1:
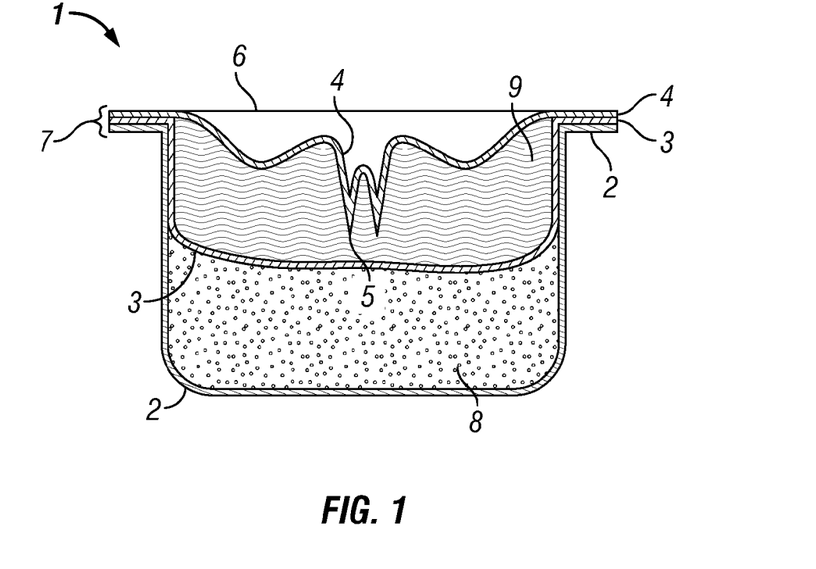
FIG. 1 is a schematic drawing of a structure for the cold pack.

Reference is made now to FIG. 1 which describes the general construction of the cold pack (1).

The cold pack includes two small containers—outer (2) and inner (3), perhaps made of plastic material by vacuum forming. The lower cavity of container (2) contains the material (8) that has an endothermic chemical reaction with water. The upper cavity (9) of container (3) contains water. Sealed cover (4) has a spring-loaded design that has at least one sharp cone (5) in order to puncture container's (3) bottom to allow the water to drain down and mix with the material in container (2). The three layers of containers (2), (3) and cover (4), are heat-sealed together and create a solid edge (7). The solid edge (7) is used to mount the cold pack on to a glucometer device. A safety sticker (6) is placed on the spring cover (4) to avoid accidental activation of the cold pack during handling and transportation.

Reference is made now to FIG. 2 which describes the assembly of the cold pack holder into the glucometer device 10.

The cold pack holder is placed into the glucometer device described in application Ser. Nos. 12/883,063 and 12/101,859. Attached motor (14) can rotate a plastic arc (16) which holds in one part cold pack (18) and the other part an aperture to allow infrared radiation to pass. The front edge of Arc (16) is positioned to be on the focal plane of the glucometer. Before the measurement commences, the motor (14) rotates the arc (16) to a position whereby the cold pack (18) touches the skin at the desired point of measurement. After a predetermined time, the motor (14) rotates the arc (16) to move the cold pack (18) away from the path of the infrared radiation while positioning the second part of the arc (16) and maintaining the desired aperture to allow the commencement of the measurement. The motor (14) is controlled by the microprocessor (12) of the glucometer device.

Figure 3:
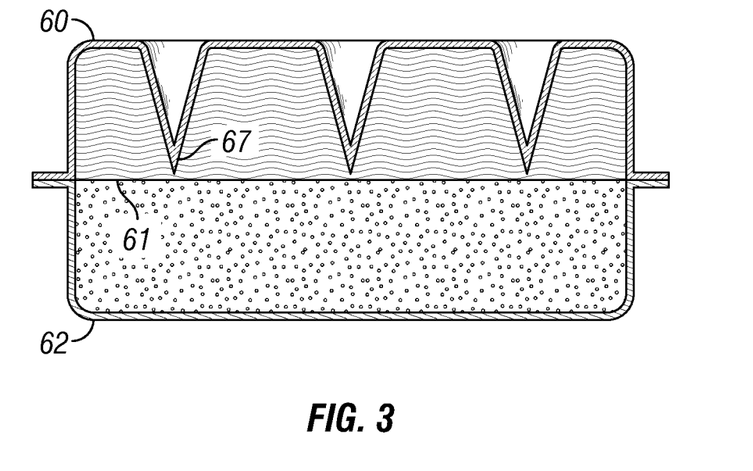
FIGS. 3, 4A-B, 5A-B, and 6 are additional embodiments of the special cold pack.

Reference is made now to FIG. 3 which shows an additional embodiment of the special cold pack.

Upper Part 60 and lower Part 62 are made from thin plastic sheet by vacuum forming, and are separated by a barrier, such as Part 61 that is made from thin aluminum foil. Upper Part 60 has one or more protrusions (i.e., dagger-like points). The three parts are sealed together by heat sealing for example. The cavity of Part 62 is filled with a material (e.g., ammonium nitrate, calcium ammonium nitrate, or urea) that has an endothermic chemical reaction with water. The cavity of upper Part 60 is filled with water. To activate, pressure is applied to the top of upper Part 60 that causes the daggers 67 to puncture the aluminum foil and allow water to mix with ammonium nitrate, calcium ammonium nitrate, or urea, thereby causing the desired cooling effect.

Figure 4A:
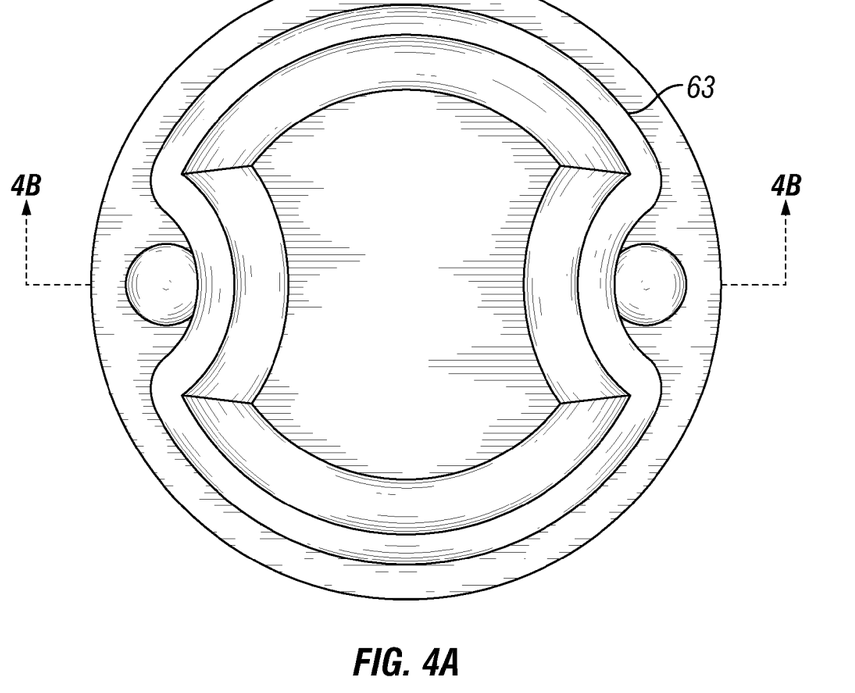
Figure 4B:
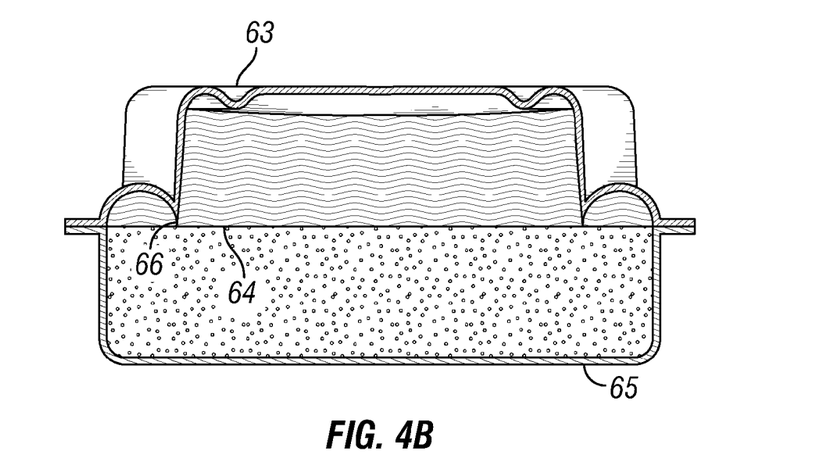

Reference is made now to FIGS. 4A and 4B which show respective top and cross-sectional views of an additional embodiment of the special cold pack.

In this embodiment, the change from the previous one (FIG. 3) is that the protruding pointed daggers 66 to puncture barrier 64 are located on the outer perimeter of upper Part 63, and they are shorter and stronger (due to having been made by vacuum forming) than what was described in the previous embodiment. Upper Part 63 is sealed to lower Part 65. The steps to activate the special cold pack are the same as described above.

Figure 5A:
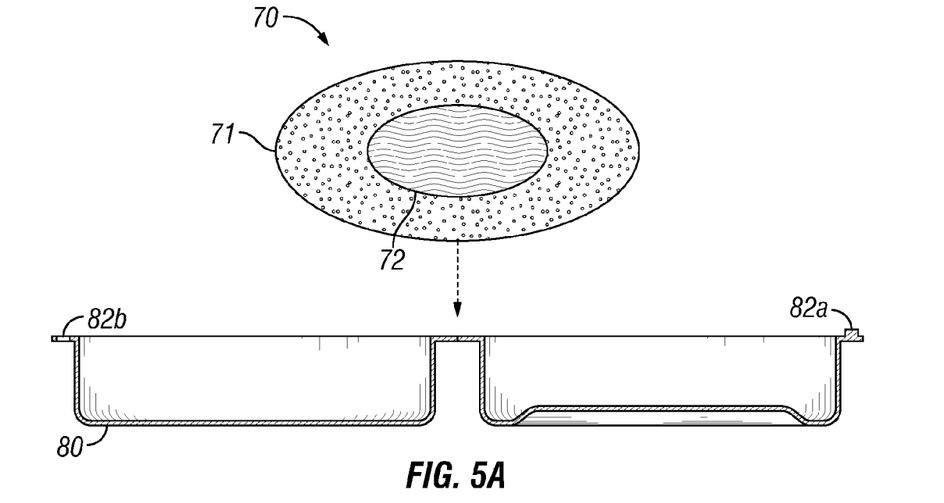
Figure 5B:
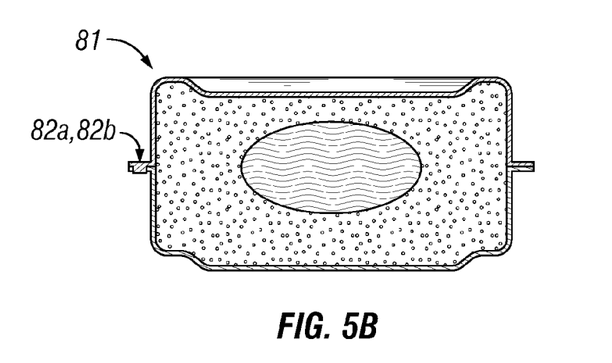

Reference is made now to FIG. 5 which shows an additional embodiment of the cold pack.

It shows a new concept for a cold pack that will fit into the non-invasive glucose meter. A cold pack 70 has an outer plastic bag 71 that contains ammonium nitrate, calcium ammonium nitrate, or urea and an inner plastic bag 72 that contains water and has perforations so that it will easily tear. The volume of cold pack 70 fits into the shell 80, which may be made by vacuum forming. To activate the cold pack 70, pressure is applied briefly to the outer bag 71 that tears the inner bag 72 and mixes the water with ammonium nitrate, calcium ammonium nitrate, or urea. The cold pack is then inserted into shell 80. Shell 80 is snapped shut into the assembly 81 shown in FIG. 5B using snap halves 82a and 82b.

Figure 6:
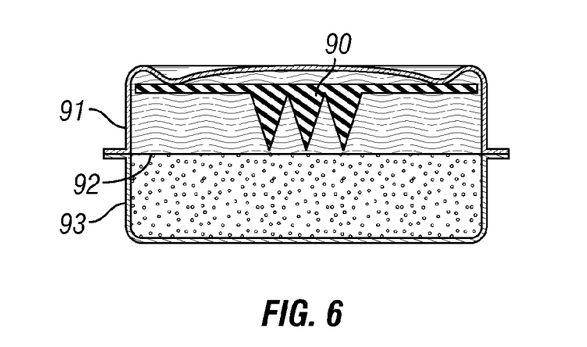

Reference is made now to FIG. 6 which shows an additional embodiment of the cold pack.

The embodiment of FIG. 6 differs from the previous embodiments by having an additional plastic Part 90 made by injection molding. When pushing the upper part 91 of the cold pack, Part 90 moves down like a piston and punctures the barrier part 92, such as aluminum foil, and then pushes the water down into the lower part 93 containing the ammonium nitrate, calcium ammonium nitrate, or urea.

Figure 7A:
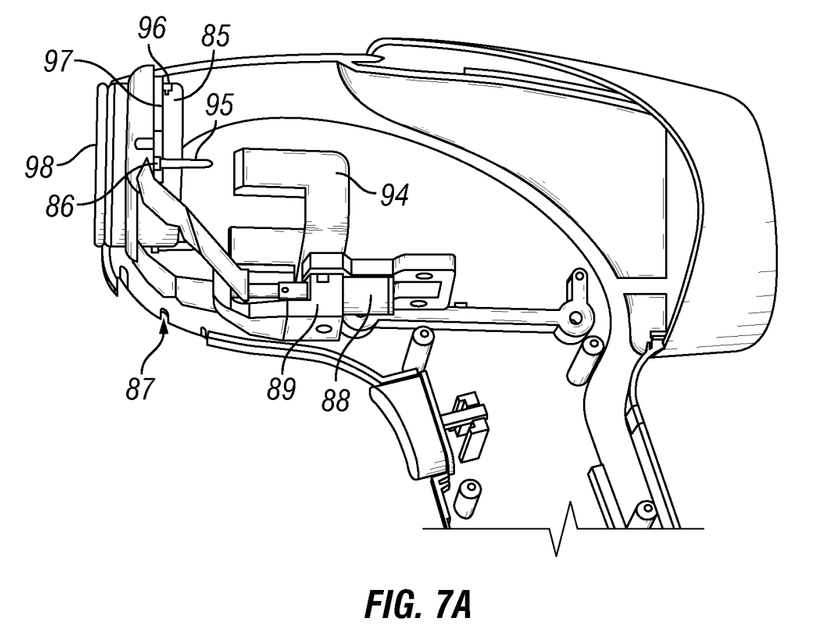
Figure 7B:
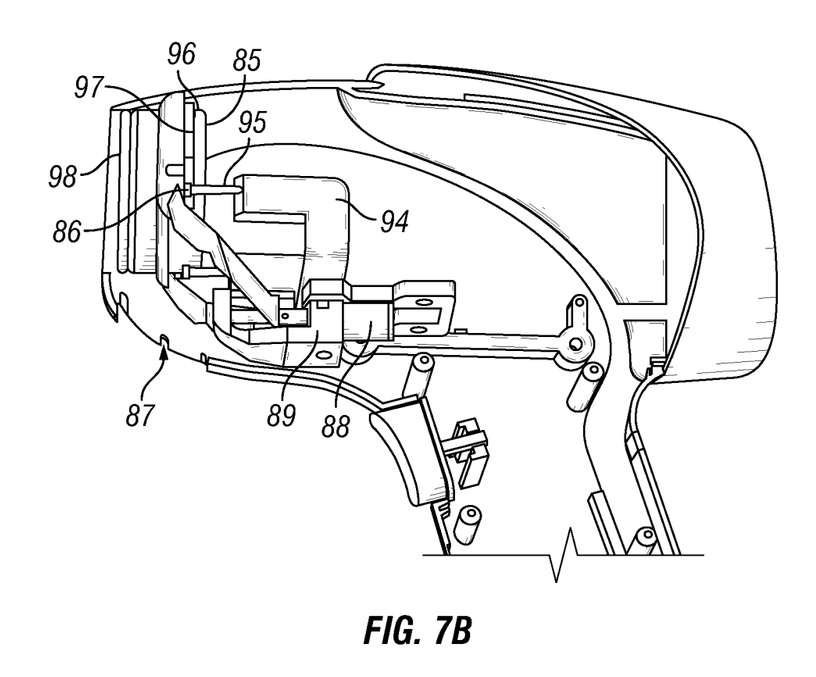

Reference is made now to FIGS. 7 (a) and (b) which shows an additional embodiment of the cold pack holding mechanism.

Cold pack 85 is inserted into position through opening 87 in the plastic housing, and is locked into place by mechanical arms 86. Mechanical arms 86 are spring loaded by spring 97 that is mounted onto pin 96. In this position, the front end 98 of cold pack 85 is at the focal plane of the device and touches the subject's skin at the desired area. Motor 88 through mechanical arm 89 is responsible for moving the cold pack to the front or back of the mechanism.

In FIG. 7 (b), the position where the motor retracts the cold pack to the back position is shown. Pin 95 hits mechanical arm 94 during the movement and is pushed sideways by the front slope of the mechanical arm 94 which pushes mechanical arm 86 to move aside. The cold pack then falls and clears the infrared radiation pathway to the optical system. The process of the cold pack front-end holding mechanism guarantees and maintains the placement of the optical system in focus.

FIGS. 8A-D show an additional embodiment of the special cold pack where 180 is the cold pack including outer bag 181 made of plastic material, such as PVC. This bag holds ammonium nitrate, calcium ammonium nitrate, or urea or another endothermic or dissolved material and the internal plastic bag 182 that holds water. Internal bag 182 usually has perforations to allow easy tear by applying force.

Figure 8A:
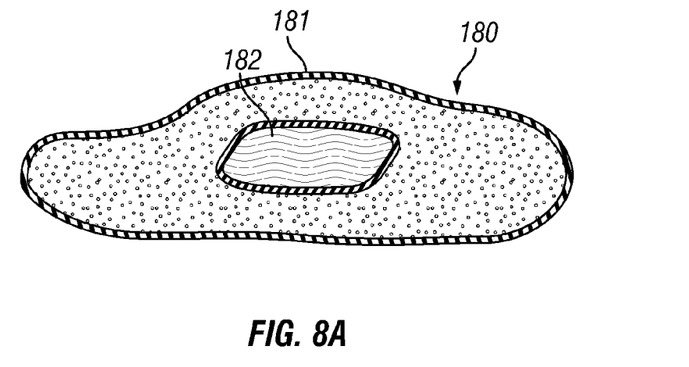
FIGS. 8A-D show an additional embodiment of the cold pack where the cold pack is separate from the shell.
Figure 8B:
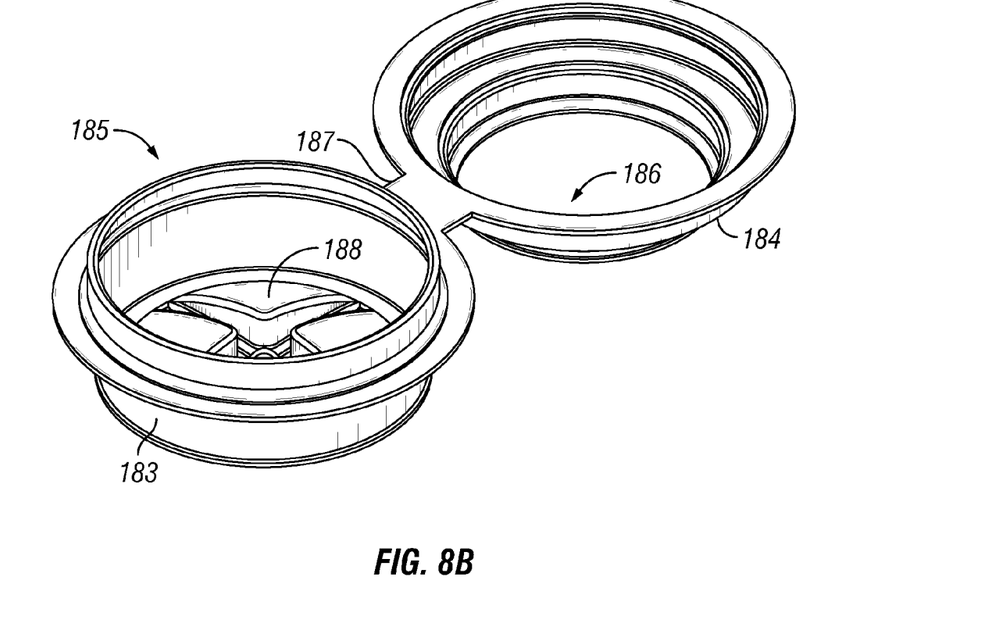
Figure 8C:
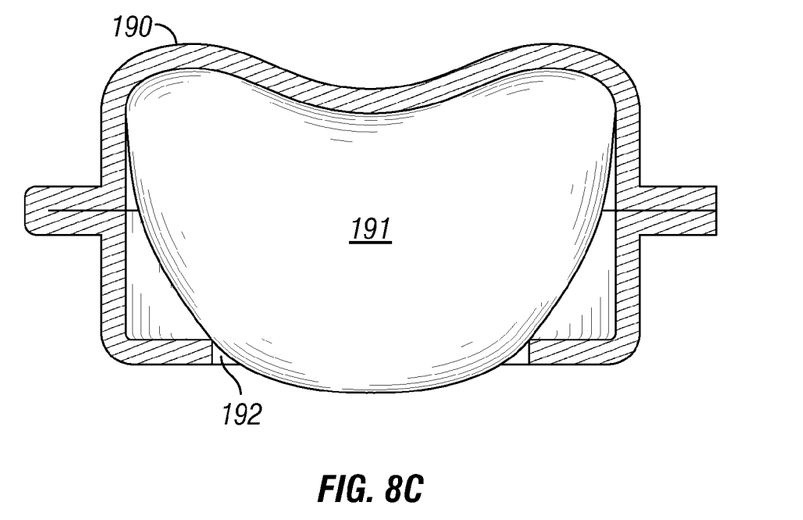
Figure 8D:
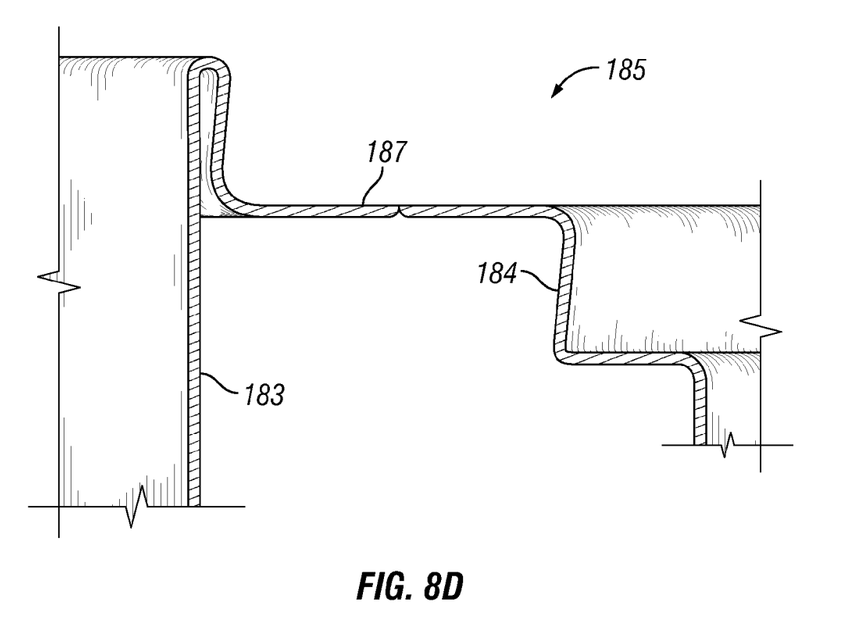

After applying force and shaking cold pack 180, it is inserted into shell 185 shown in FIG. 8B. Shell 185 may be made by vacuum forming from PVC. Shell 185 has an opening 186 and a concave part 188 to press the cold pack into the opening. Shell 185 is one piece with a base 183, a lid 184, a pivot 187, and snap 189 that allow it to close as is shown in 8C. The closed shell 190 has inside cold pack 191 that can touch directly the forehead through opening 192.

In compliance with the statute, the embodiments have been described in language more or less specific as to structural and methodical features. It is to be understood, however, that the embodiments are not limited to the specific features shown and described. The embodiments are, therefore, claimed in any of their forms or modifications within the proper scope of the appended claims appropriately interpreted in accordance with the doctrine of equivalents.

TABLE OF REFERENCE NUMERALS FOR FIGURES

| | | | | | |
|---|---|---|---|---|---|
| 1 | cold pack | 85 | cold pack | 180 | cold pack |
| 2 | container | 86 | arms | 181 | outer bag |
| 3 | container | 87 | opening | 182 | internal bag |
| 4 | cover | 88 | motor | 183 | base |
| 5 | cone | 89 | arm | 184 | lid |
| 6 | safety sticker | 94 | arm | 185 | shell |
| 7 | edge | 95 | pin | 186 | opening |
| 8 | endothermic material | 96 | pin | 187 | pivot |
| | | 97 | spring | 188 | concave part |
| 9 | cavity | 98 | front end | 189 | snap |
| 10 | glucometer device | | | 190 | closed shell |
| 12 | microprocessor | | | 191 | activated cold pack |
| 14 | motor | | | 192 | opening |
| 16 | arc | | | | |
| 18 | cold pack | | | | |
| 60 | upper part | | | | |
| 61 | barrier part | | | | |
| 62 | lower part | | | | |
| 63 | upper part | | | | |
| 64 | barrier part | | | | |
| 65 | lower part | | | | |
| 66 | dagger | | | | |
| 67 | dagger | | | | |
| 70 | cold pack | | | | |
| 71 | outer bag | | | | |
| 72 | inner bag | | | | |
| 80 | shell | | | | |
| 81 | assembly | | | | |
| 82a/b | snap | | | | |
| 90 | piston part | | | | |
| 91 | upper part | | | | |
| 92 | barrier part | | | | |
| 93 | lower part | | | | |

What is claimed is:

1. A measurement apparatus comprising:
    a cooling device including two separated, different substances exhibiting an endothermic reaction when combined to decrease a temperature of the cooling device;
    a combining mechanism of the cooling device configured to combine the two different substances;
    a contacting mechanism configured to contact an assay surface of a subject's body with the cooling device and to decrease a temperature of the assay surface of a subject's body with the cooling device to a lower temperature, the contacting mechanism including:
        a spring-loaded, first mechanical arm configured to retain the cooling device and to position a front end of the cooling device at a focal plane of the measurement apparatus;
        a motor connected to the first mechanical arm by a second mechanical arm and configured to retract the cooling device retained by the first mechanical arm to a back position inside the measurement apparatus; and a pin connected to the first mechanical arm and configured to contact a third mechanical arm when the cooling device reaches the back position and to push aside the first mechanical arm, releasing the cooling device;

a temperature measurement device configured to measure a temperature of the assay surface of a subject's body during an increase of the temperature from the lower temperature;

an infrared radiation detector configured to measure infrared radiation emitted from or absorbed by the assay surface of a subject's body during the temperature increase; and a data processor configured to determine a rate of temperature change of the assay surface and configured to determine a concentration of a substance in the subject's body using the measured temperature of the assay surface, the measured infrared radiation, and the rate of temperature change.

2. The apparatus of claim 1 wherein the cooling device comprises:

a rigid, plastic shell including a sealed lower cavity containing a material that reacts endothermically with water and a sealed upper cavity containing water;

one or more sharp daggers in the upper cavity; and a spring-loaded puncturing mechanism configured to return the sharp daggers to their original position after being depressed and puncturing the lower cavity.

3. A measurement apparatus comprising:

a cooling device including:

two separated, different substances exhibiting an endothermic reaction when combined to decrease a temperature of the cooling device;

a rigid shell including a base, a lid that attaches to the base, and an opening through the lid;

a flexible bag having a size and shape configured to fit within the shell with the lid closed and expose the bag above the opening through the lid, the bag containing a first of the two different substances;

a combining mechanism of the cooling device configured to combine the two different substances and including a pouch within the flexible bag containing a second of the two different substances, the pouch being configured to release the second substance into the first substance upon opening the pouch;

a contacting mechanism configured to contact an assay surface of a subject's body with the cooling device and to decrease a temperature of the assay surface of a subject's body with the cooling device to a lower temperature;

a temperature measurement device configured to measure a temperature of the assay surface of a subject's body during an increase of the temperature from the lower temperature;

an infrared radiation detector configured to measure infrared radiation emitted from or absorbed by the assay surface of a subject's body during the temperature increase; and a data processor configured to determine a concentration of a substance in the subject's body using the measured temperature of the assay surface and the measured infrared radiation.

4. The apparatus of claim 3 wherein the first substance is selected from among ammonium nitrate, calcium ammonium nitrate, urea, and combinations thereof.

5. The apparatus of claim 3 further comprising a mounting edge on opposing sides of the rigid shell, the mounting edge being configured to mount the cooling device to the measurement apparatus.

6. The apparatus of claim 5 wherein the mounting edge comprises a circumferential flange of the lid and a circumferential flange of the base, the two flanges coinciding with one another with the lid closed.

7. The apparatus of claim 3 wherein the base and the lid are one-piece and the cooling device further comprises a pivot connecting the base to the lid, a concave part of the base configured to press the flexible bag into the opening through the lid, and a snap configured to close the lid to the base.

8. A measurement method comprising:

using a cooling device including two separated, different substances exhibiting an endothermic reaction when combined;

using a combining mechanism of the cooling device, combining the two different substances;

using the combined substances, decreasing a temperature of the cooling device;

retaining the cooling device in a spring-loaded, first mechanical arm and positioning a front end of the cooling device at a focal plane of the measurement apparatus;

contacting an assay surface of a subject's body with the cooling device and decreasing a temperature of the assay surface of the subject's body with the cooling device to a lower temperature;

after decreasing the temperature, a motor connected to the first mechanical arm by a second mechanical arm retracting the cooling device retained by the first mechanical arm to a back position inside the measurement apparatus; and a pin connected to the first mechanical arm contacting a third mechanical arm when the cooling device reaches the back position and pushing aside the first mechanical arm, releasing the cooling device;

after decreasing the temperature of the assay surface using the cooling device, using a temperature measurement device and measuring a temperature of the assay surface of the subject's body during an increase of the temperature of the assay surface from the lower temperature;

using an infrared radiation detector and measuring infrared radiation emitted from or absorbed by the assay surface during the temperature increase from the lower temperature; and using a data processor, determining a rate of temperature change of the assay surface and determining a concentration of a substance in the subject's body using the measured temperature of the assay surface, the measured infrared radiation, and the rate of temperature change.

9. The method of claim 8 wherein the cooling device comprises:

a rigid, plastic shell including a sealed lower cavity containing a material that reacts endothermically with water and a sealed upper cavity containing water;

one or more sharp daggers in the upper cavity; and a spring-loaded puncturing mechanism returning the sharp daggers to their original position after being depressed and puncturing the lower cavity.

10. A cooling device comprising:
two separated, different substances exhibiting an endothermic reaction when combined to decrease a temperature of the cooling device;
a rigid shell including a base, a lid that attaches to the base, and an opening through the lid;
a flexible bag having a size and shape configured to fit within the shell with the lid closed and expose the bag above the opening through the lid, the bag containing a first of the two different substances;
a combining mechanism of the cooling device configured to combine the two different substances and including a pouch within the flexible bag containing a second of the two different substances, the pouch being configured to release the second substance into the first substance upon opening the pouch; and
a mounting edge on opposing sides of the rigid shell, the mounting edge being configured to mount the cooling device to a measurement apparatus.

11. The cooling device of claim 10 wherein the mounting edge comprises a circumferential flange of the lid and a circumferential flange of the base, the two flanges coinciding with one another with the lid closed.

12. A measurement method comprising:
using a cooling device including:
two separated, different substances exhibiting an endothermic reaction when combined;
a rigid shell including a base, a lid that attaches to the base, and an opening through the lid; and
a flexible bag having a size and shape fitting within the shell with the lid closed and exposing the bag above the opening through the lid, the bag containing a first of the two different substances;
using a combining mechanism of the cooling device, combining the two different substances, the combining mechanism including a pouch within the flexible bag containing a second of the two different substances, the pouch releasing the second substance into the first substance upon opening the pouch;
using the combined substances, decreasing a temperature of the cooling device;
contacting an assay surface of a subject's body with the cooling device and decreasing a temperature of the assay surface of the subject's body with the cooling device to a lower temperature;
after decreasing the temperature of the assay surface using the cooling device, using a temperature measurement device and measuring a temperature of the assay surface of the subject's body during an increase of the temperature of the assay surface from the lower temperature;
using an infrared radiation detector and measuring infrared radiation emitted from or absorbed by the assay surface during the temperature increase from the lower temperature; and
using a data processor, determining a rate of temperature change of the assay surface and determining a concentration of a substance in the subject's body using the measured temperature of the assay surface, the measured infrared radiation, and the rate of temperature change.

13. The method of claim 12 wherein the first substance is selected from among ammonium nitrate, calcium ammonium nitrate, urea, and combinations thereof.

14. The method of claim 12 further comprising mounting the cooling device to the measurement apparatus using a mounting edge on opposing sides of the rigid shell.

15. The method of claim 14 wherein the mounting edge comprises a circumferential flange of the lid and a circumferential flange of the base, the two flanges coinciding with one another with the lid closed.

16. The method of claim 12 wherein the base and the lid are one-piece and the cooling device further comprises a pivot connecting the base to the lid, a concave part of the base pressing the flexible bag into the opening through the lid, and a snap closing the lid to the base.

* * * * *